United States Patent [19]
Takeda et al.

[11] Patent Number: 5,255,686
[45] Date of Patent: Oct. 26, 1993

[54] CONTINUOUS NONINVASIVE BLOOD PRESSURE MEASURING APPARATUS AND METHOD

[75] Inventors: Sunao Takeda; Hideo Ozawa; Mitsushi Hyogo; Yoshinobu Nakae, all of Tokyo, Japan

[73] Assignee: Nihon Kohden Corporation, Tokyo, Japan

[21] Appl. No.: 907,795

[22] Filed: Jul. 2, 1992

[30] Foreign Application Priority Data

Jul. 4, 1991 [JP] Japan .................... 3-189559

[51] Int. Cl.$^5$ ............................ A61B 5/00
[52] U.S. Cl. ..................... 128/681; 128/682
[58] Field of Search ............... 128/677-686

[56] References Cited

U.S. PATENT DOCUMENTS

| | | | |
|---|---|---|---|
| 4,607,641 | 8/1986 | Fukushima | 128/680 |
| 4,664,126 | 5/1987 | Link | 128/680 |
| 4,747,412 | 5/1988 | Yamaguchi | 128/680 |

*Primary Examiner*—Lee S. Cohen
*Assistant Examiner*—Robert L. Nasser, Jr.
*Attorney, Agent, or Firm*—Sughrue, Mion, Zinn, Macpeak & Seas

[57] ABSTRACT

In a continuous noninvasive blood pressure measuring apparatus, a systolic pressure, diastolic pressure, and mean arterial pressure for calibration are measured according to the output of a pressure sensor, a cuff pressure is set lower than the diastolic pressure by a cuff pressure control section, and a reference pulse wave is obtained from the arithmetic means of a plurality of cuff pulse waves. A CPU calculates the peak value and the bottom value of the reference pulse wave, and a cuff pressure mean value corresponding to the D.C. component of the reference pulse wave, and further calculates coefficients which are used to allow the peak value, bottom value and cuff pressure mean value thus obtained to correspond to correspond to the systolic pressure, diastolic pressure, and mean arterial pressure, respectively. The CPU calculates according to the output of a temperature sensor a cuff pressure temperature compensation value for compensating for an amount of variation of the cuff pressure which varies with the temperature of the cuff. In addition, the CPU, while compensating the cuff pressure, which is read continuously, with the cuff pressure temperature compensation value, continuously calculates a blood pressure by utilizing the cuff pressure thus compensated, and the coefficients provided by the coefficient calculating section, and the cuff pulse waves read continuously.

2 Claims, 6 Drawing Sheets

FIG. 6

CONTINUOUS NONINVASIVE BLOOD PRESSURE MEASURING APPARATUS AND METHOD

BACKGROUND OF THE INVENTION

This invention relates to a blood pressure measuring apparatus for continuously measuring a blood pressure in a noninvasive mode, and more particularly to a continuous noninvasive blood pressure measuring apparatus having means for compensating a cuff pressure which varies with the temperature of the air in the cuff.

In order to monitor an arterial pressure for a long period of time, there are available two methods. One of the methods is an invasive blood pressure measuring method which is practiced with a pressure transmitting tube or pressure sensor inserted into the blood vessel, and the other is a noninvasive blood pressure measuring method in which a sensor is set outside the body under examination; that is, the living body is not hurt at all. In one example of the noninvasive blood pressure measuring method, the diameter of a blood vessel, which varies with the pressure in it, is measured, and the blood pressure is calculated from the diameter thus measured. Hereinafter, the noninvasive blood pressure measuring method in which a blood pressure is measured from the variation in diameter of a blood vessel, will be described.

In the noninvasive blood pressure measuring method, with a cuff put on the brachium (or upper arm), a mean arterial pressure, a systolic pressure, and a diastolic pressure are measured according to the ordinary oscillometric method, and those pressures are employed calibrating values. Thereafter, the cuff pressure is set to a pressure, for instance 20 mmHg, lower than the diastolic pressure, and then the cuff is closed. Under this condition, the following coefficients are determined: First, a coefficient is obtained which is used for allowing the D.C. component of the cuff pressure provided immediately after the closing of the cuff to correspond to the mean arterial pressure. Next, several pulses provided through the cuff are detected and averaged to form a pulse waveform, and a coefficient is obtained which is used for allowing the peak value of the pulse waveform thus formed to correspond to the systolic pressure, and similarly a coefficient is obtained which is used for allowing the bottom value of the pulse wave to correspond to the diastolic pressure. The D.C. variation of the cuff pressure reflects variations in mean arterial pressure, and the cuff pulse waveform reflects variations both in systolic pressure and in diastolic pressure. Hence, the arterial pressure waveform can be continuously calculated by using the D.C. variation in pressure of the closed cuff, the measured values of the cuff pulse waveform, and the coefficients thereof.

In the above-described conventional noninvasive blood pressure measuring method, the cuff is closed, so that the cuff pressure changes with the temperature of the air in the cuff. Therefore, it is difficult to determine whether the variation in cuff pressure is due to the variation in mean arterial pressure or whether it is due to the variation in cuff temperature. As a result, sometimes the blood pressure calculated includes a serious error.

Heretofore, this diffuculty is eliminated as follows: When the blood pressure calculated is deviated by a certain value from the value which is obtained by the initial calibration measurement, then the calibration measurement is carried out again to renew the mean arterial pressure, systolic pressure and diastolic pressure thereby to calculate new coefficients.

Hence, immediately after the blood pressure measuring operation starts; that is, when the cuff temperature is abruptly raised by the body temperature of a person under examination, it is necessary to perform the calibration measurement frequently (for instance every three to five minutes). This will displease him.

SUMMARY OF THE INVENTION

Accordingly, an object of this invention is to solve the above-described problems accompanying a conventional noninvasive blood pressure measuring method. More specifically, an object of the invention is to provide a continuous noninvasive blood pressure measuring apparatus which is able to measure a blood pressure with high accuracy, being free from the difficulty that it is necessary to frequently perform the calibration measurement.

The foregoing object of the invention has been achieved by the provision of a continuous noninvasive blood pressure measuring apparatus which, according to the invention, comprises:

a cuff to be put on the body of a person under examination;

cuff pressure control means for controlling a pressure of the cuff;

a pressure sensor for detecting a pressure of the cuff;

a temperature sensor for detecting a temperature of the cuff;

calibration measurement means for allowing the cuff pressure control means to control the cuff pressure, and measuring a systolic pressure, a diastolic pressure and a mean arterial pressure for calibration measurement according to the output of the pressure sensor;

reference pulse wave forming section which allows the cuff pressure control means to set the cuff pressure to lower than the diastolic pressure, and obtains the arithmetic mean of a plurality of cuff pulse waves provided by the pressure sensor, to form a reference pulse wave, and calculates the peak value and the bottom value of the reference pulse wave and a cuff pressure mean value corresponding to the D.C. component of the reference pulse wave;

coefficient calculating section for calculating coefficients which are used to allow the peak value, bottom value, and cuff pressure mean value provided by the reference pulse wave forming section to correspond to the systolic pressure, diastolic pressure, and means arterial pressure provided by the calibration measurement means, respectively;

cuff pressure temperature compensation value calculating section for calculating according to the output of the temperature sensor a cuff pressure temperature compensation value for compensating for an amount of variation of the cuff pressure which varies with the temperature of the cuff; and a blood pressure calculating section which compensates the cuff pressure, which is read continuously, with the cuff pressure temperature compensation value provided by the cuff pressure temperature compensation value calculating section, and continuously calculates a blood pressure by utilizing the cuff pressure thus compensated, the coefficients provided by the coefficient calculating section, and the cuff pulse waves read continuously.

In the apparatus thus organized, the cuff pressure temperature compensation value calculating section provides the cuff pressure temperature compensation value to compensate for the amount of variation in cuff pressure which is due to the change in temperature of the cuff, and therefore the blood pressure calculated by the blood pressure calculating section is high in accuracy.

Hence, the calibration measurement can be made at much longer time intervals.

DETAILED DESCRIPTION OF THE PREFERRED EMBODIMENT

Figure 1:
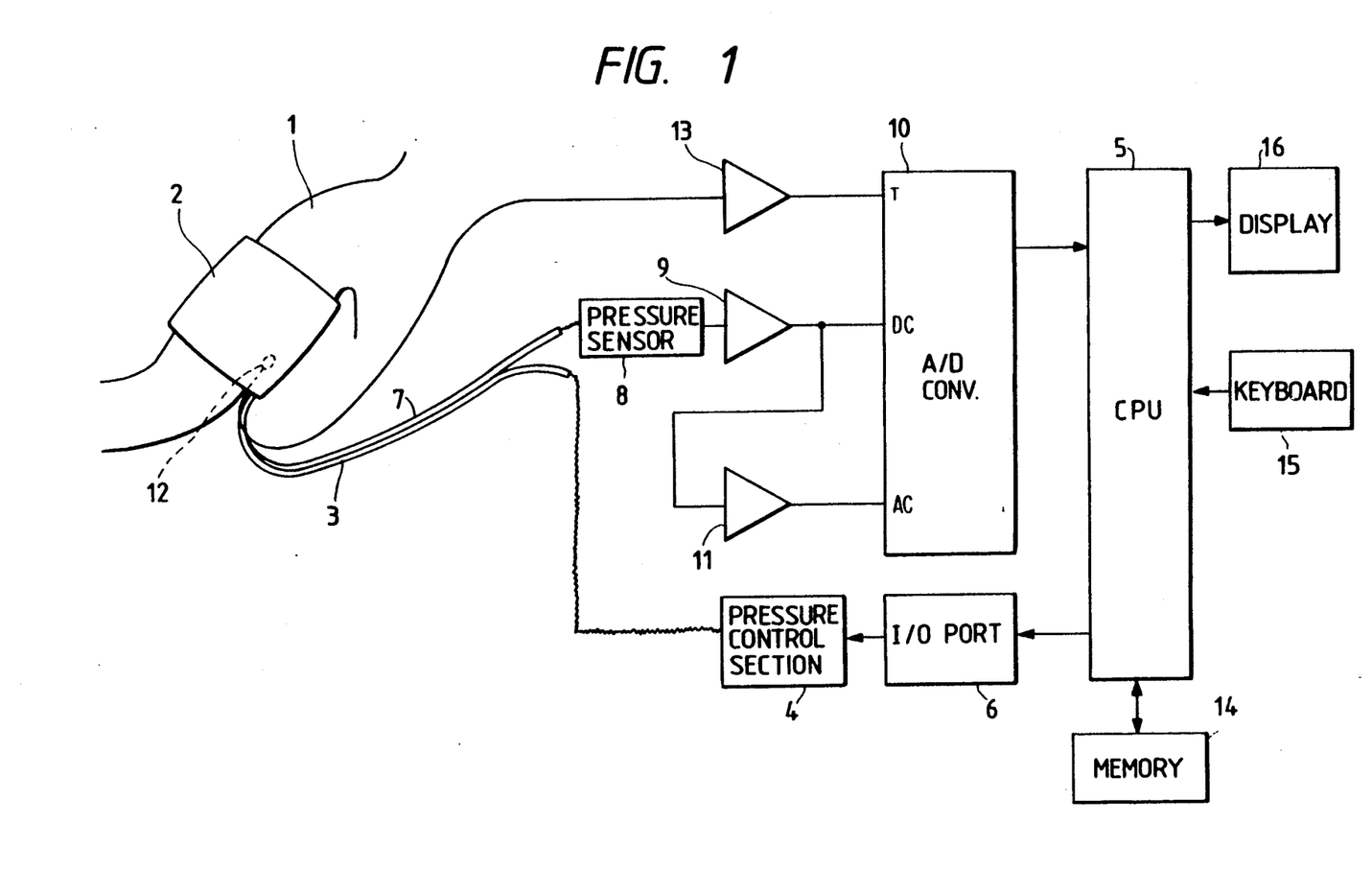
FIG. 1 is a block diagram, partly as an explanatory diagram, showing the arrangement of a continuous noninvasive blood pressure measuring apparatus according to this invention.

An example of a continuous noninvasive blood pressure measuring apparatus according to this invention will be described with reference to the accompanying drawings in detail. FIG. 1 is a block diagram showing the arrangement of the blood pressure measuring apparatus according to the invention.

As shown in FIG. 1, a cuff 2 put on the brachium of a person under examination is coupled through an air hose 3 to a pressure control section 4. The pressure control section 4 comprising a pressurizing pump and a pressure control valve sets a cuff pressure. A central processing unit 5 (hereinafter referred to as "a CPU 5", when applicable) applies a pressure setting control signal through an input/output port (I/O port) 6 to the pressure control section 4.

A pressure sensor 8 connected through an air hose 7 to the cuff 2 detects a cuff pressure. The detection output of the pressure sensor is amplified by a pressure sensor amplifier 9, the output of which is applied, as a cuff pressure D.C. component, to an analog-to-digital converter 10 (hereinafter referred to as "an A/D converter 10", when applicable). On the other hand, the pulse wave component of the output of the amplifier 9 is amplified by an A.C. amplifier 11, the output of which is applied, as a cuff pressure A.C. component, to the A/D converter 10. The cuff pressure D.C. component and the cuff pressure A.C. component are converted into digital signals, which are applied to the CPU 5.

In order to measure the temperature of the air in the cuff, a temperature sensor 12 is built in the cuff 2. The detection output of the temperature sensor 12 is amplified by a temperature sensor amplifier 13, the output of which is converted by the A/D converter 10 into a digital signal. The digital signal is applied to the CPU 5.

The blood pressure measuring apparatus further comprises: a memory circuit 14 including a read-only memory (ROM) and a random access memory (RAM). An operating program has been stored in the ROM. Measurement data, coefficients (described later), and a cuff pressure temperature compensation value (described later) are temporarily stored in the RAM.

The CPU 5 is connected to a keyboard 15, through which a measurement starting instruction or a measurement ending instruction, and identification data for a person under examination may be inputted.

The CPU 5 is further connected to a display unit 16, on which a blood pressure measured is continuously displayed.

The CPU 5 includes a calculating section for calibration measurement, a reference pulse wave forming section, a coefficient calculating section, a cuff-pressure-compensating-valve calculating section, and a blood pressure calculating section.

Figure 2:
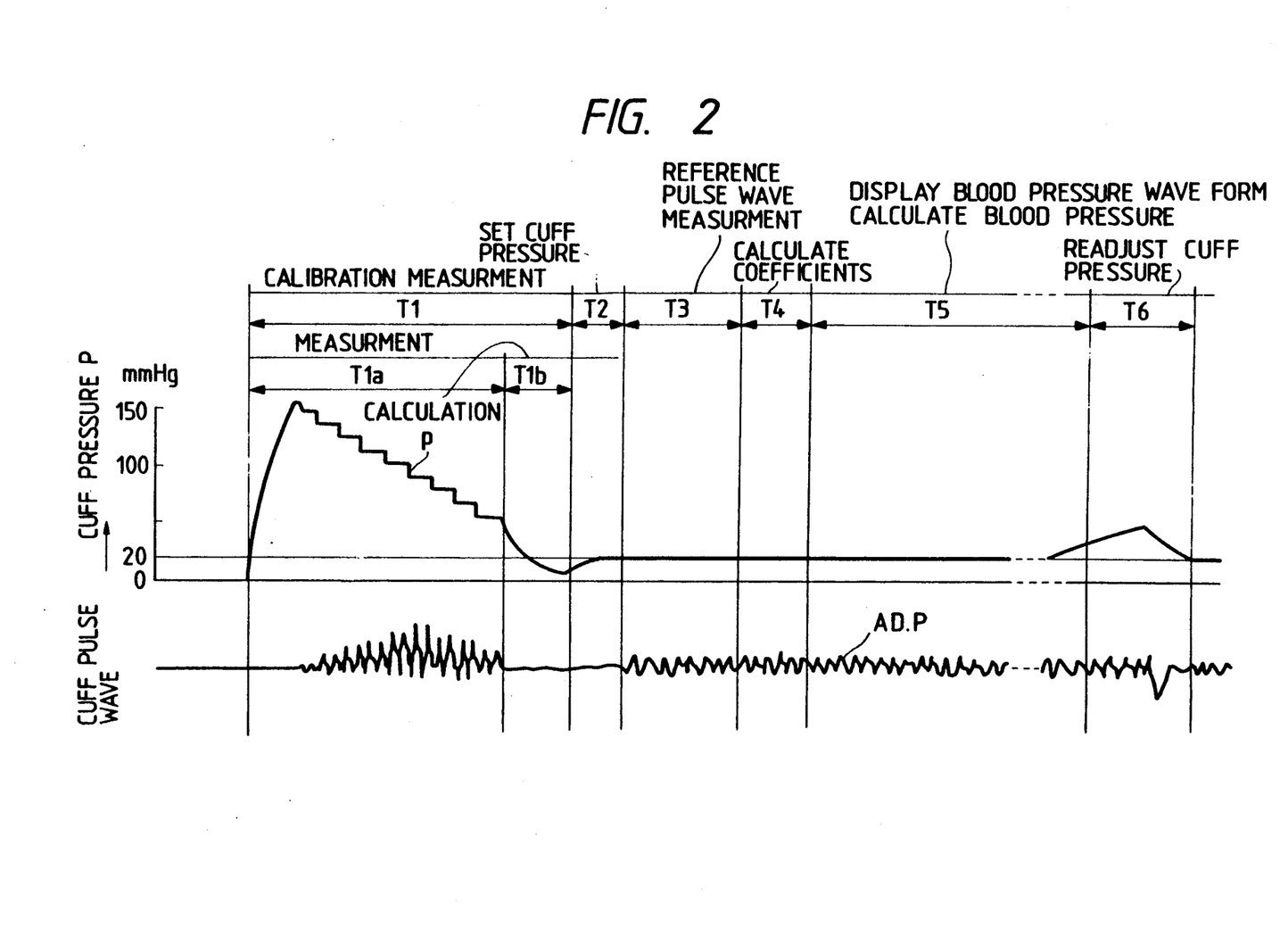
FIG. 2 is a waveform diagram for a description of the operation of the blood pressure measuring apparatus according to the invention.
Figure 3:
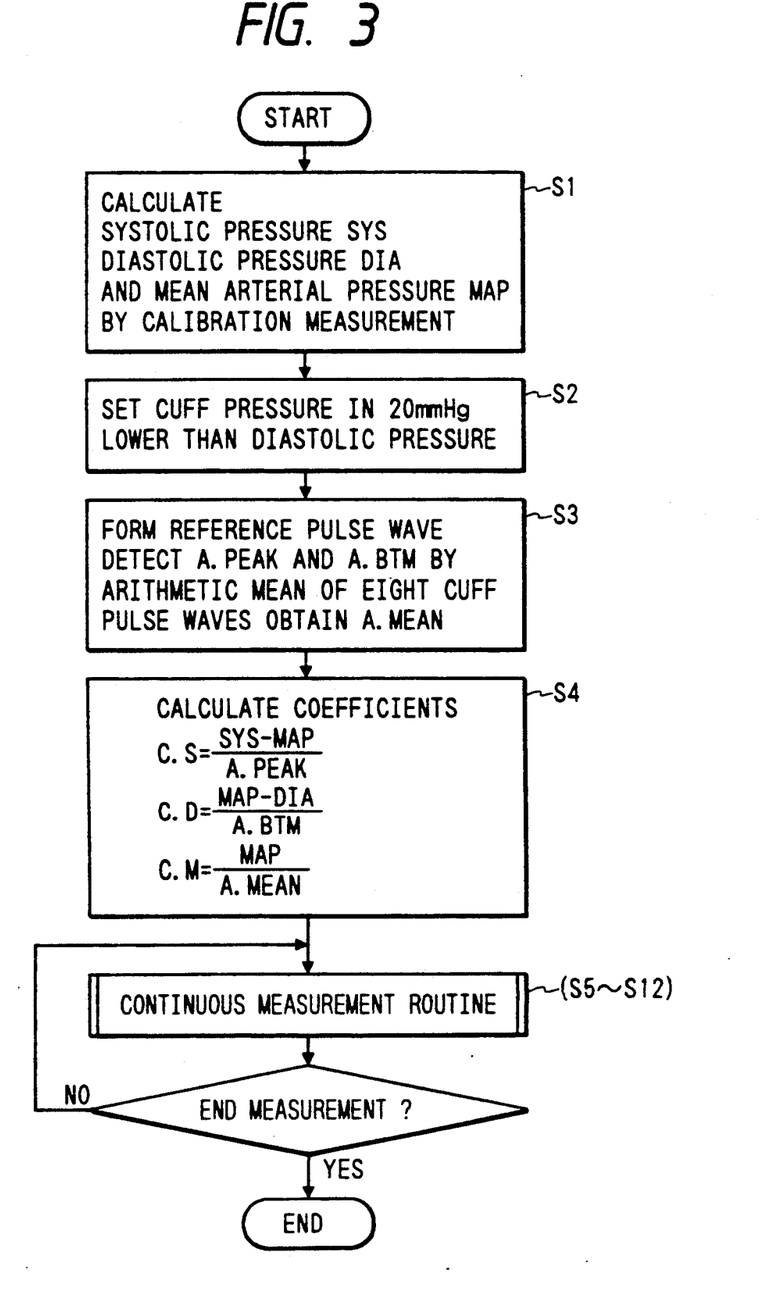
FIGS. 3 and 4 are flow charts for a description of the operation of the blood pressure measuring apparatus according to the invention.

The operation of the continuous noninvasive blood pressure measuring apparatus thus organized will be described with reference to a waveform diagram of FIG. 2, and flow charts of FIGS. 3 and 4.

First, in order to perform a calibration measurement during the time period T1, the cuff pressure P is increased to higher than the systolic pressure, and then while being decreased stepwise, it is measured according to the oscillometric method (the time period T1a). Thereafter, during the following time period T1b, the CPU 5 calculates the systolic pressure SYS, the diastolic pressure DIA, and the mean arterial pressure MAP. The above-described operations correspond to Step S1 in FIG. 3.

Next, in the following time period T2, the cuff pressure control section 4 sets the cuff pressure P, for instance, to 20 mmHg which is lower than the diastolic pressure (Step S2).

Figure 5:
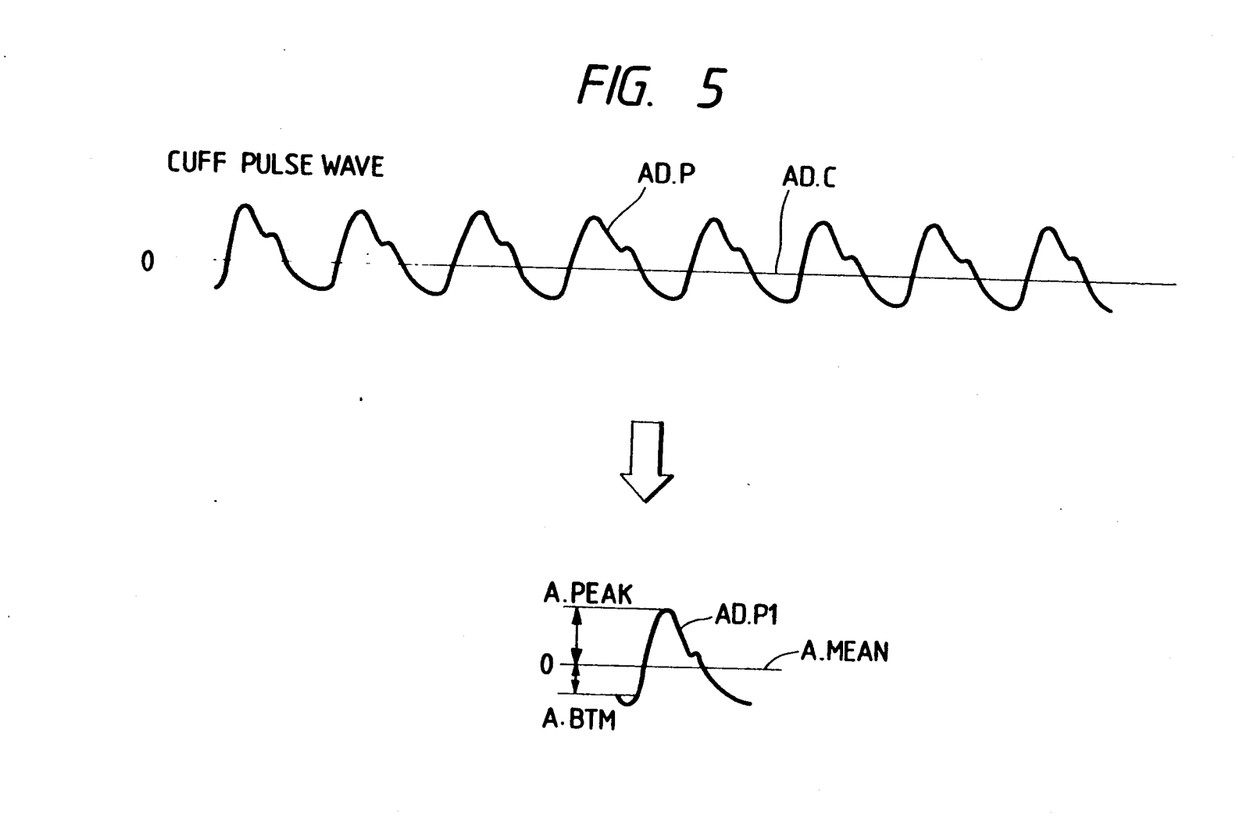
FIG. 5 is a waveform diagram showing a reference pulse wave which is obtained from the arithmetic mean of a plurality of cuff pulse waves.

In the next time period T3, the CPU 5 reads a cuff pulse wave AD.P which is detected after the cuff pressure P has been set to 20 mmHg, and samples, for instance, eight (8) cuff pulse waves AD.P and obtains the arithmetic mean of them, thereby to form a reference pulse wave AD.P1. The CPU 5 further operates to detect a peak value A.PEAK and a bottom value A.BTM from the reference pulse wave AD.P1 thus formed, and to average the D.C. component AD.C of cuff pressure to obtain a mean value A.MEAN (Step S3).

Thereafter, in the following time period T4, the CPU 5 calculates the following three coefficients C.S, C.D, and C.M. (Step S4). The coefficient C.S is to allow the peak value A.PEAK to correspond to the systolic pressure SYS. The coefficient C.D is to allow the bottom value A.BTM to correspond to the diastolic pressure DIA. The coefficient C.M is to allow the mean value A.MEAN to correspond to the mean arterial pressure MAP.

Figure 4:
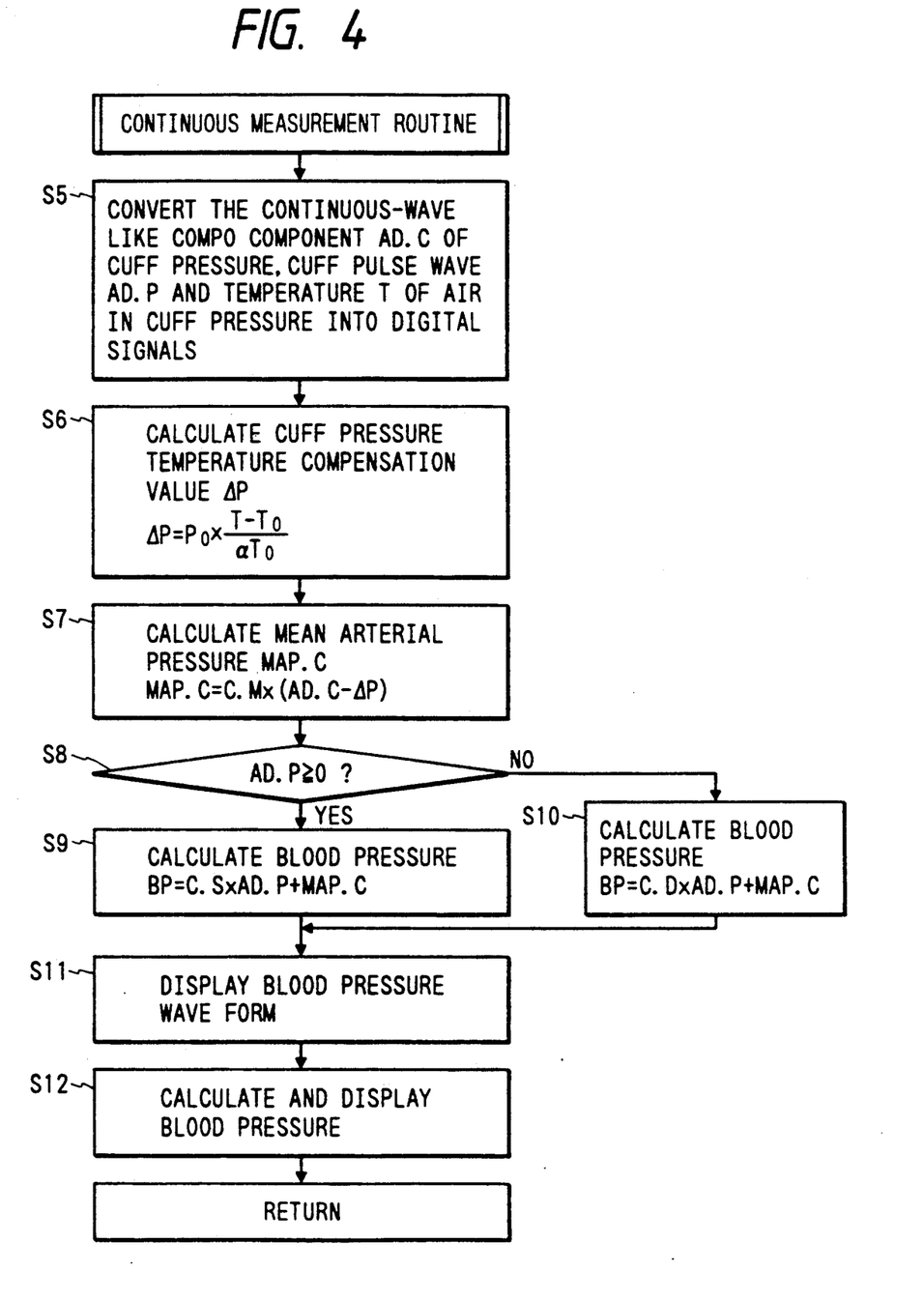

Next, a continuous measurement routine is effected which, as shown in FIG. 4, is to continuously measure a blood pressure (the time period T5). In the continuous measurement routine, first, under the condition that the cuff pressure P is set to 20 mmHg, the D.C. component AD.C of the cuff pressure, the cuff pulse wave AD.P (the A.C. component of the cuff pressure), and the temperature T of the air in the cuff (hereinafter referred to as "a cuff air temperature", when applicable) are subjected to analog-to-digital conversion; that is, they are converted into digital signals, which are applied to the CPU 5 (Step S5).

Thereafter, in order to compensate the cuff pressure P which changes as the cuff air temperature is raised by the body temperature of the person under examination, a cuff pressure temperature compensation value ΔP is calculated from the following equation by the CPU 5 (Step S6):

$$\Delta P = P_0 \times (T - T_0)/\alpha T_0$$

where $P_0$ and $T_0$ are the initial cuff pressure and the initial cuff air temperature provided when the coefficients C.S, C.D, and C.M are obtained, respectively, and α is the parameter concerning the compliance of the cuff 2 which depends on the material of the cuff and the way of putting the cuff on the arm.

Next, the D.C. component AD.C of the cuff pressure is compensated by the cuff pressure temperature compensation value ΔP, and the CPU 5 utilizes the cuff pressure D.C. component thus compensated (AD.C−ΔP) and the coefficient C.M to calculate a mean arterial pressure MAP.C from the following equation (Step S7):

$$MAP.C = C.M \times (AD.C - \Delta P)$$

Thereafter, the CPU 5 determines whether the cuff pulse wave AD.P thus read is a positive component more than zero, or whether it is a minus component not more than zero (Step S8).

When it is determined that the cuff pulse wave AD.P is more than zero, the CPU 5 utilizes the coefficient C.S, the cuff pulse wave AD.P and the temperature-compensated mean arterial pressure MAP.C to calculate a blood pressure BP from the following equation (Step S9):

$$BP = C.S \times AD.P + MAP.C$$

When it is determined that the cuff pulse wave AD.P is not more than zero, the CPU 5 utilizes the coefficient C.D, the cuff pulse wave AD.P and the temperature-compensated mean arterial pressure MAP.C to calculate a blood pressure BP from the following equation (Step S9):

$$BP = C.D \times AD.P + MAP.C$$

Figure 6:
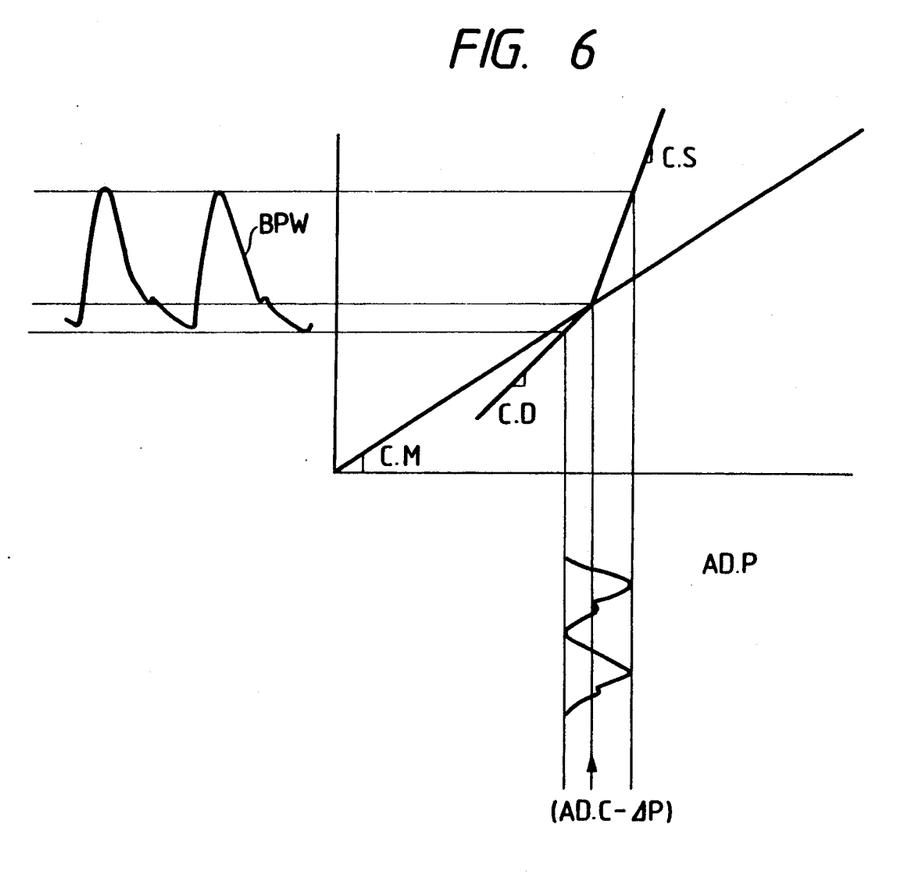
FIG. 6 is an explanatory diagram for a description of an operation of obtaining a continuous blood pressure wave from an input cuff pulse wave.

FIG. 6 shows a blood pressure waveform BPW which is obtained by multiplying the cuff pulse wave AD.P inputted continuously and the D.C. component of the temperature-compensated cuff pressure by the coefficients C.S, C.D and C.M.

The blood pressure waveform BPW thus obtained is displayed on the display unit 16 (Step S11), and the systolic pressure and the diastolic pressure are calculated, and displayed on the displayed unit 16 (Step S12).

Thereafter, this continuous measurement routine (Steps S5 through S12) is repeatedly executed. If, during the execution of the routine, the cuff pressure P comes out of a range of 20±0.8 mmHg, the cuff pressure P is readjusted (the time period T6).

The blood pressure measuring operation can be ended by inputting the blood pressure measurement ending instruction through the key board (Steps S13 and S14).

In the continuous noninvasive blood pressure measuring apparatus of the invention, as was described above, the cuff pressure increased with the body temperature of a person under examination is temperature-compensated. Therefore, the calibration measurement to renew the coefficients C.S, C.D and C.M may be performed at time intervals of from thirty (30) minutes to one (1) hour or more. This will reduce the burden of the person under examination.

In the above-described embodiment, the temperature sensor is built inside the cuff 2; however, the invention is not limited thereto or thereby. That is, it may be built in the material of the cuff 2, or it may be set on the outer surface of the cuff.

As was described above, in the blood measuring apparatus of the invention, the cuff pressure is compensated which varies as the temperature of the air in the cuff put on a person under measurement is changed by his body temperature. Hence, the calibration measurement can be made at much longer time intervals, which will reduce the unpleased burden of the person under measurement. In addition, with the apparatus, a blood pressure can be measured continuously with high accuracy for a long period of time.

What is claimed is:

1. A continuous noninvasive blood pressure measuring apparatus for use in measuring blood pressure of a subject, the apparatus comprising:
   a cuff to be put on the subject;
   cuff control means for controlling a pressure of said cuff;
   pressure sensor means for detecting a pressure of said cuff and for outputting a plurality of cuff pulse waves representative thereof;
   temperature sensor means for detecting a temperature of said cuff;
   calibration and measurement means for calibrating said pressure of said cuff and measuring a systolic pressure, a diastolic pressure and a mean arterial pressure in accordance with an output of said pressure sensor means, wherein said systolic pressure, said diastolic pressure and said means arterial pressure are used for calibration;
   reference pulse wave forming means for calculating an arithmetic means of a plurality of cuff pulse waves provided by said pressure sensor means to form a reference pulse wave and for calculating a peak value, a bottom value and a cuff pressure mean value corresponding to a continuous wave component of said reference pulse wave;
   coefficient calculating means for calculating coefficients to cause correspondence between said peak value, said bottom value, said cuff pressure mean value, as calculated by said reference pulse wave forming means, with said systolic pressure, said diastolic pressure, and said mean arterial pressure, respectively, as calculated by said calibration measurement means;
   cuff pressure temperature compensation value calculating means for calculating a cuff pressure temperature compensation value in accordance with an output of said temperature sensor means, said cuff pressure temperature compensating value for use in compensating for an amount of variation of said cuff pressure with variation in temperature of said cuff; and
   a blood pressure calculating means for compensating said cuff pressure with said cuff pressure temperature compensation value calculated by said cuff pressure temperature compensation value calculating means, and for continuously calculating a blood pressure by utilizing said cuff pressure thus compensated, said coefficient calculated by said coefficient calculating section, and said plurality cuff pulse waves.

2. A method of measuring a continuous noninvasive blood pressure of a subject, said method comprising the steps of: setting a cuff on the subject;

performing a calibration measurement including the steps of:

increasing a cuff pressure to higher than a systolic pressure;

calculating a systolic pressure SYS, a diastolic pressure DIA, and a mean arterial pressure MAP;

setting a cuff pressure to a predetermined value which is lower than said diastolic pressure;

reading a cuff pressure pulse wave ADP and obtaining an arithmetic mean of several cuff pulse waves to form a reference pulse wave ADP1;

detecting a peak value APEAK and a bottom value ABTM from said reference pulse value ADP1 and averaging a DC component ADC of cuff pressure to achieve a mean value AMEAN;

calculating coefficients CS, CD, and CM in such manner that said coefficient CS causes said peak value APEAK to correspond to a systolic pressure SYS, said coefficient CD to correspond to said bottom value BTM of a diastolic pressure DIA, and said coefficient CM to correspond to said means value AMEAN of said mean arterial pressure MAP;

converting said DC component ADC, said cuff pulse wave ADP, and a temperature T of an air in said cuff into digital signals;

calculating a cuff pressure temperature compensation value $\Delta P$, where $$\Delta P = P_o \times (T - T_o)/\alpha T_o$$

where, $P_o$ is an initial cuff pressure and $T_o$ is an internal cuff air temperature when said coefficient CS, CD and CM are obtained, and $\alpha$ is a parameter related to said cuff;

calculating a temperature-compensated mean arterial pressure MAPC from $$MAPC = CM \times (ADC - \Delta P);$$

determining whether said cuff pulse wave ADP is a positive component more than zero or whether it is a minus component not more than zero;

when said cuff pulse wave ADP is a positive component more than zero, calculating a systolic blood pressure BP, where $$BP = C.S \times AD.P + MAP.C,$$

when said cuff pulse wave ADP is a minus component not more than zero, calculating a diastolic blood pressure BP, where $$BP = CD \times ADP + MAPC;$$

and calculating a blood pressure waveform BPW by multiplying said cuff pulse wave ADP inputted continuously and a component of a temperature compensated cuff pressure using said coefficient CS, CD and CM.

* * * * *